(12) United States Patent
Durkee et al.

(10) Patent No.: US 6,748,803 B1
(45) Date of Patent: Jun. 15, 2004

(54) LIQUID MEASUREMENT SYSTEM AND SHARED INTERFACE APPARATUS FOR USE THEREIN

(75) Inventors: Scott Robert Durkee, New Haven, VT (US); Bradley F. Eid, Greenwood, IN (US)

(73) Assignee: Simmonds Precison Products, Inc., Charlotte, NC (US)

( * ) Notice: Subject to any disclaimer, the term of this patent is extended or adjusted under 35 U.S.C. 154(b) by 0 days.

(21) Appl. No.: 09/511,419

(22) Filed: Feb. 22, 2000

(51) Int. Cl.[7] .............................................. G01F 23/00
(52) U.S. Cl. ................... 73/290 V; 73/290; 73/290 B; 73/706; 73/646; 324/664; 367/87; 367/903; 310/319
(58) Field of Search .......................... 310/319; 367/87, 367/903; 73/646, 706, 290, 290 V, 290 B; 324/664

(56) References Cited

U.S. PATENT DOCUMENTS

| | | | |
|---|---|---|---|
| 4,487,065 A | * 12/1984 | Carlin et al. | 73/290 |
| 4,815,323 A | * 3/1989 | Ellinger et al. | 73/290 |
| 4,853,694 A | * 8/1989 | Tomecek | 340/621 |
| 5,594,352 A | * 1/1997 | Johnson | 324/664 |
| 5,606,513 A | * 2/1997 | Louwagie et al. | 340/621 |
| 6,236,142 B1 | * 5/2001 | Durkee | 310/319 |
| 6,272,922 B1 | * 8/2001 | Stevens et al. | 310/319 |

FOREIGN PATENT DOCUMENTS

| | | |
|---|---|---|
| EP | 0813044 A2 | 6/1997 |
| WO | WO 99/32858 | 7/1998 |

* cited by examiner

*Primary Examiner*—Daniel S. Larkin
*Assistant Examiner*—André K. Jackson
(74) *Attorney, Agent, or Firm*—David R. Percio; Calfee, Halter & Griswold LLP

(57) ABSTRACT

A liquid measurement system including interface apparatus for sharing the excitation and signal processing of an ultrasonic transonic transducer and temperature measuring device remotely located at a liquid container is disclosed. The interface apparatus includes a common conduction path coupled to both of the ultrasonic transducer and the temperature device for conducting first excitation signals to the ultrasonic transducer and the corresponding echo signals therefrom, and for conducting second excitation signals to the temperature measuring device and the response signals therefrom, and an interface circuit for governing the conduction of the first and second excitation signals over the common conduction path from their generating sources and for providing a balanced interface for receiving both of the echo signals and response signals from the common conduction path. In one embodiment, the liquid measurement signal includes a processor that is coupled to the interface circuit for receiving the echo signals and the response signals therefrom for determining liquid level in the container based on the received signals.

30 Claims, 2 Drawing Sheets

LIQUID MEASUREMENT SYSTEM AND SHARED INTERFACE APPARATUS FOR USE THEREIN

BACKGROUND OF THE INVENTION

The present invention is directed to liquid measuring systems in general, and more specifically, to a liquid measurement system including interface apparatus for sharing the excitation and signal processing of an ultrasonic transducer and temperature measuring device remotely located at a liquid container.

Present liquid measurement systems of the ultrasonic variety utilize an ultrasonic transducer disposed at the liquid container for measuring the level of liquid in the container. The ultrasonic transducer is excited to generate ultrasonic pulses directed at the surface of the liquid level and for receiving echoes from the surface of the liquid level that are converted into corresponding echo signals. These systems generally include a temperature measuring device, like a resistance temperature device or RTD, for example, disposed at the container in contact with the liquid in close proximity to the ultrasonic transducer. When the RTD is excited, it generates a response signal representative of the temperature of the liquid that is used along with the echo signals for the determination of the liquid level in the container.

While the ultrasonic transducer and its temperature measuring device are located at the liquid container, the apparatus for exciting and signal processing each such device is generally located remotely from the container. Where the liquid container is a fuel tank on-board an aircraft, the exciting and processing apparatus may be located anywhere from twenty to three hundred feet from the fuel tank. In addition, each device includes its own dedicated apparatus and cabling and on-board commercial aircraft in particular, there may be thirty to forty or more of these devices. Thus, in the aircraft industry, this individually dedicated apparatus and cabling represents a heavy burden in volume and weight as well as cost of labor, maintenance and fuel consumption. Accordingly, it is desirable, especially for aircraft applications, to reduce the dedicated apparatus and cabling for each such device.

SUMMARY OF THE INVENTION

In accordance with the present invention, a liquid measurement system includes interface apparatus for sharing the excitation and signal processing of an ultrasonic transducer remotely located therefrom at a liquid container and of a temperature measuring device disposed in close proximity to the ultrasonic transducer for measuring the temperature of tile liquid threat. The ultrasonic transducer is excited to generate ultrasonic pulses directed at the surface of the liquid level in the container and for receiving ultrasonic echoes from the liquid level that are converted into corresponding echo signals. The temperature measuring device is excited to generate a response signal representative of the temperature of the liquid in close proximity to the ultrasonic transducer. The interface apparatus includes a first means for generating first excitation signals for tile ultrasonic transducer, second means for generating second excitation signals for the temperature measuring device, a common conduction path coupled to both of the ultrasonic transducer and the temperature measuring device for conducting the first excitation signals to the ultrasonic transducer and the corresponding echo signals therefrom, and for conducting the second excitation signals to the temperature device and the response signals therefrom, and an interface circuit coupled between the first and second means and the common conduction path for governing the conduction of the first and second excitation signals over the common conduction path and for providing a balanced interface for receiving both of the echo signals and response signals from the common conduction path. In accordance with another aspect of the present invention, the liquid measurement system includes a processing means coupled to the interface circuit for receiving the echo signals and the response signals therefrom for determing liquid level in the container based on the received signals.

DESCRIPTION OF THE PREFERRED EMBODIMENT

Figure 1:
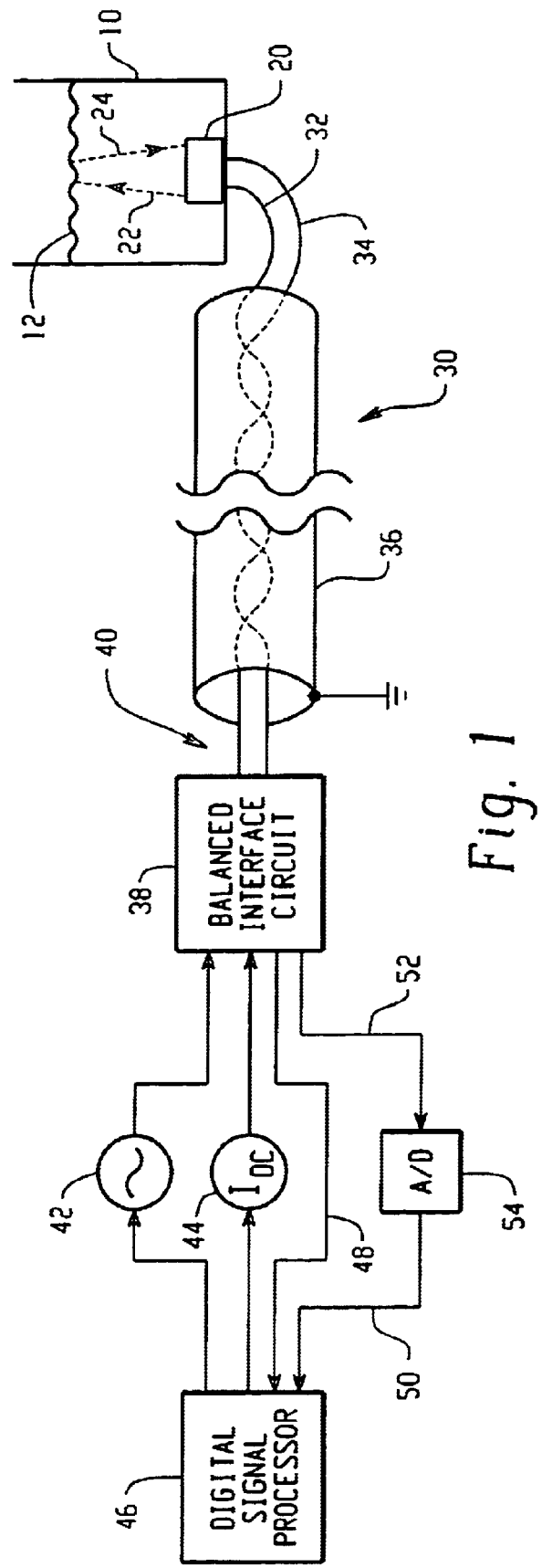
FIG. 1 is a block diagram schematic of a liquid measurement system suitable for embodying the principles of the present invention.

Referring to FIG. 1, a liquid container is shown at 10 containing liquid at a level 12. By way of example for the purpose of describing the present embodiment, the container 10 may be an aircraft fuel tank containing aircraft fuel at the level 12. In the present embodiment, an ultrasonic transducer 14 and a temperature measuring device 16 are included in a common transducer assembly 20 (refer to FIG. 2 for greater detail) that is disposed at the container 10. While it is preferred that the ultrasonic transducer 14 and temperature measuring device 16 be contained in a common assembly, it is understood that the present invention need not be so limited. It is desired however to have the temperature measuring device 16 disposed at the container in contact with the liquid in close proximity to the ultrasonic transducer.

The ultrasonic transducer 14 which may be of the piezo ceramic variety including a PZT (lead zirconate titanate) crystal, for example, is excited by pulsed alternating current (AC) signals of a relatively high frequency that may be on the order of one (1) megahertz (MHz), for example, to generate ultrasonic pulses 22 directed at the liquid level 12. In addition, the ultrasonic transducer 14 is operative to receive echoes 24 from the liquid level and convert them into corresponding echo signals. Ultrasonic transducers generally include a negative impedance component that acts to reduce power to the device at the operating excitation frequency thereof In the present embodiment, a tuning inductor 18 is coupled in series with the ultrasonic transducer 14 (shown in FIG. 2) and is of a positive reactive impedance value at the operating frequency to negate the negative reactive impedance component of the transducer 14 in order to maximize power thereto.

The temperature measuring device 16 which may be a resistance temperature device or RTD, for example, is disposed in parallel with the transducer 14 in the present embodiment. In this arrangement, it is preferred that the RTD be essentially non-inductive, that is less than five(5) microhenries, for example, in order not to introduce stray inductance to the circuit. For this purpose, a semiconductor-based RTD of the type manufactured by Kulite Semiconductor Products, Inc. would be suitable. The resistance of the RTD may be on the order of 1–10 KiloOhms for the present embodiment. In this parallel circuit arrangement, the RTD 16 may also function as a bleed resistor to the transducer 14 to prevent charge build-up on the capacitive component integral thereto. Another resistor (not shown) of a resistance on the order of one or more MegaOhms may also be coupled in parallel with the transducer 14 to ensure against such charge build-up.

A common conduction path 30 is coupled to both of the ultrasonic transducer 14 and RTD 16 for conducting first excitation signals to the transducer 14 and corresponding echo signals therefrom, and for conducting second excitation signals to the RTD 16 and response signals therefrom. In the present embodiment, the path 30 is a twisted pair of wires 32 and 34 that are coupled across the parallel circuit arrangement of the transducer 14 and RTD 16 at the container 10. The path 30 may include a shield 36 covering the twisted wire pair which may be grounded at one end, preferably the end remote from the container 20, or at both ends as the application dictates.

Figure 2:
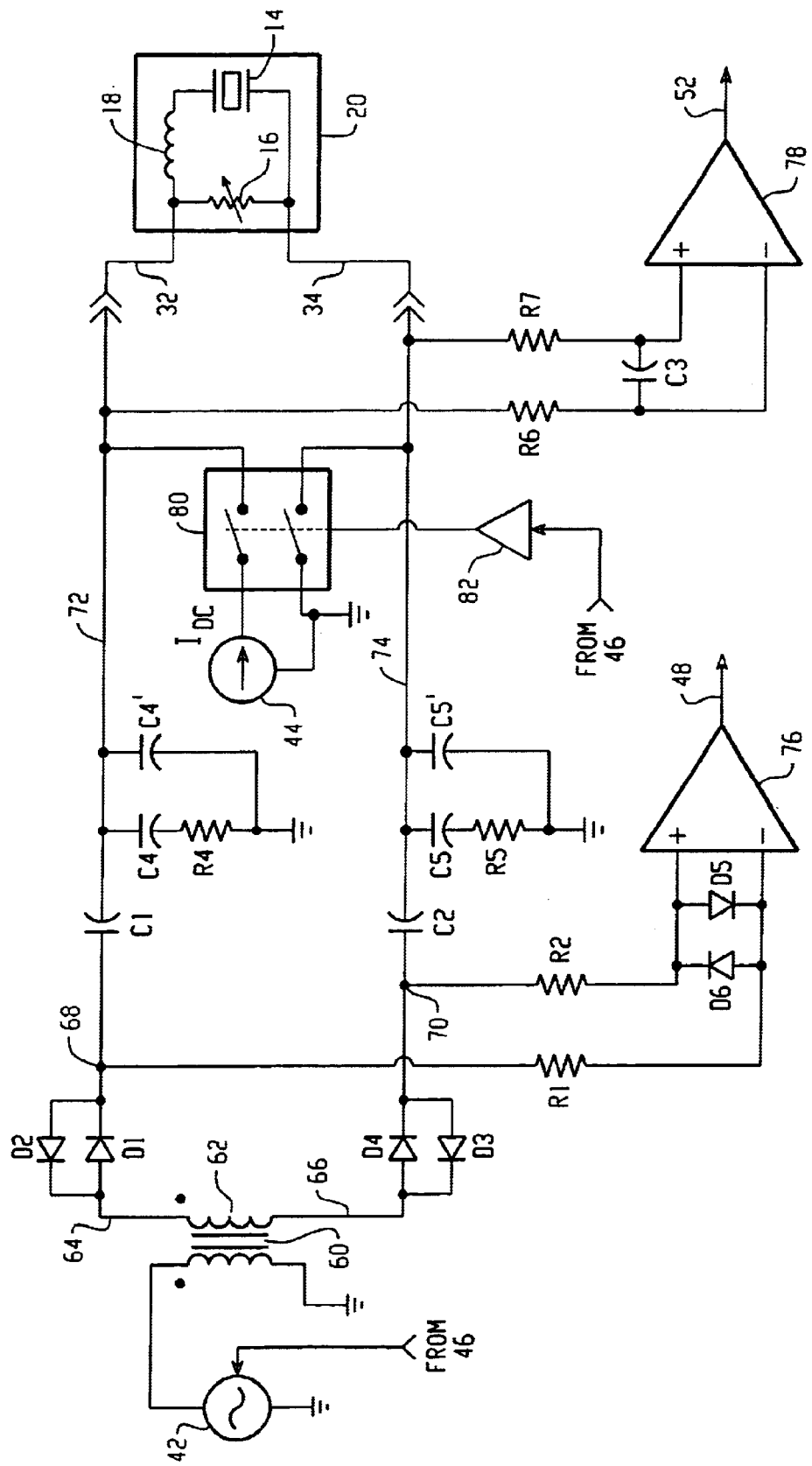
FIG. 2 is a circuit schematic diagram of interface apparatus suitable for use in the embodiment depicted by FIG. 1.

An interface circuit 38 that is shown in greater detail in the schematic of FIG. 2 is located remotely from the container 10 and coupled to the remote end 40 of the conduction path 30. Also remotely located from the container 10 are a pulsed controlled oscillator circuit 42 for generating the first excitation signals for the transducer 14 and a precision current source 44 for generating the second excitation signals for the RTD 16. Both of the circuits 42 and 44 that may be of a conventional design well known to those skilled in the pertinent art are coupled to the interface circuit 38. The interface circuit 30 is operative to govern the conduction of the first and second excitation signals over the path 30 and to provide a balanced interface for receiving over the path 30 both of the echo signals and response signals from the devices 14 and 16, respectively. The operation of the interface circuit 38 will become more apparent from the description of the circuit embodiment of FIG. 2.

In the present embodiment, a digital signal processor 46 that may be of the type manufactured by Texas Instruments under the model number TMS320C32X, for example, operates to control the pulsed operation of the oscillator 42 and the operation of the source 44 through the interface circuit 38. The processor 46 is coupled to the interface circuit 38 for receiving the echo signals over signal line 48 and the response signals over data lines 50 and is operative to determine Linder program control the level of the liquid in the container 10 based on the received signals. Since the operation of the processor 46 is digital, the analog response signals form the RTD 16 over signal line 52 are digitized by a conventional analog-to-digital converter (A/D) 54 that may also be controlled by the processor 46 in the present embodiment. The algorithms executed by the processor 46 for determing the liquid level from the echo signals and temperature response signals are well known to all those skilled in the pertinent art and for this reason need not be described in detail for the present embodiment. More specifically, in the present embodiment, the oscillator circuit 42 is gated to produce a pulse of one to sixteen sinusoidal cycles of one megahertz frequency at a burst frequency on the order of one to eight hertz. However, it is understood that the interpulse period and duration of the pulse may vary during operation based on the level of liquid in container 10.

Referring now to FIG. 2, the oscillator circuit 42 is coupled to a primary side of a step up transformer 60 of the interface circuit 38. The transformer 60 of the present embodiment is of the type having a ferrite torroidal core designed particularly for RF applications and has a winding ratio of typically one to eight. Accordingly, a differential pulsed AC signal having a high peak-to-peak voltage on the order of ninety to one-hundred and ten volts is induced across the secondary winding 62 of the transformer 60. Back to back diodes D1 and D2 are coupled in series to one end 64 of the secondary winding 62. In a balanced arrangement, back to back diodes D3 and D4 are coupled to the other end 66 of the secondary winding 62. Capacitor C1 is coupled in series with the diode pair D1, D2 to form a circuit node 68 and for balance, capacitor C2 is coupled in series with the diode pair D3, D4 to form a circuit node 70. For the present embodiment, the diodes may be 1N4148s and the capacitors may be of a value on the order of one microfarad. Wire 32 of the twisted pair is connected to the other side of capacitor C1 at a circuit node 72 and for balance, the other wire 34 of the pair is connected to the other side of capacitor C2 at a circuit node 74.

A differential video amplifier 76 is coupled across the circuit nodes 68 and 70 through resistors R1 and R2, respectively. Back to back diodes D5, D6 are coupled across the inputs of the amplifier 76 to protect the input stage thereof against overvoltage damage from the pulsed high voltage AC excitation signal induced across the secondary winding 62. The output of amplifier 76 may be coupled to the processor 46 over signal line 48 as shown in FIG. 1. In the present embodiment, the amplifier 76 may be of the type manufactured by MAXIM bearing model number MAX 436, for example, that has a bandwidth around two hundred and seventy-five megahertz. In addition, an instrumentation amplifier 78 which may be of the type manufactured by Analog Devices bearing model number AD521, for example, is coupled across the circuit nodes 72 and 74 through the resistors R6 and R7, respectively. A capacitor C3 is coupled across the inputs of the amplifier 78 to filter out the high frequency first excitation signals and associated echo signals from interfering with the operation thereof. In the present embodiment, the resistors R1 and R2 may be of a value on the order of two KiloOhms, resistors R6 and R7 may be of a value on the order of ten KiloOhms, capacitor C3 may be 0.1 microfarad and diodes D5 and D6 may be 1N4148s.

Moreover, to match the output impedance of the interface circuit 38 to that of the conduction path 30, balanced impedance matching circuits are coupled from the nodes 72 and 74 to the ground reference of the circuit 38. More specifically, a matching circuit comprising a series combination of capacitor C4 and resistor R4 in parallel with a capacitor C4' is coupled from node 72 to ground reference. And, a matching circuit comprising a series combination of capacitor C5 and resistor R5 in parallel with a capacitor C5' is coupled from the node 74 to ground reference. In the present embodiment, the values of C4 and C5 may be on the order of one microfarad, the values of the resistors R4 and R5 may be on the order of one Kilo Ohm, and the values of the capacitors C4' and C5' may be on the order of four hundred and seventy picofarads, for example.

Still further, the precision direct current (DC) current source 44 is coupled differentially to the nodes 72 and 74 through a high voltage differential switch 80. The precision current signal of the source 44 which is the second excitation signal of the present embodiment is coupled to the pole of one switch of 80 and the ground reference or return path of the source 44 is coupled to the pole of the other switch. The differential switch 80 is controlled by the processor 46 in the present embodiment through a logic buffer circuit 82. When operated in the open position., the second excitation signal is inhibited from exciting the RTD and no temperature response signal is produced thereby. In this state, the switch 80 offers a balanced high impedance to the pulsed AC excitation and associated echo signals. When operated in the closed position, the switch 80 enables excitation of the RTD by the source 44 via a low impedance path. In the present embodiment, the switch 80 may be of the type manufactured by Siliconix bearing model number DG507A, for example.

In operation, the processor 46 may control the oscillator 42 to generate pulsed AC excitation signals at around one megahertz, say on the order of five times a second to effect interpulse periods of two hundred milliseconds. Each burst or excitation pulse may include from one to sixteen cycles of the AC signal, for example. The transformer 60 steps up the excitation voltage to around ninety volts peak to peak which is passed along differentially through the balanced capacitors C1 and C2 and over the twisted wire pair 32 and 34 to excite the transducer 14. While the pulsed AC excitation signals are being generated, the switch 80 is controlled to its open position to offer a balanced high impedance to the AC excitation signal. The diodes D6 and D7 pinch off and protect the input stage of amplifier 76 against the high voltage excitations signals. Also, the capacitor C3 filters out the high voltage AC excitation signals to protect the input stage of the amplifier 78. In response to the first excitation signals, the transducer 14 generates ultrasonic pulses directed at the surface of the liquid in the tank 10. The echoes from the liquid surface are received by the transducer 14 and converted to echo signals that are conducted differentially back over the twisted wire pair of the common conduction path 30 and through the capacitors C1 and C2 to the amplifier 76. The diode pairs D1, D2 and D3, D4 prevent a short circuiting of the echo signals by blocking out the low impedance path of the transformer secondary 62 up to at least two diode voltage drops which is an adequate voltage level to be detected and amplified by the amplifier 76. In turn, the amplified echo signals are Output from the amplifier 76 over signal line 48 to the processor 46 for use in determining the level of the fuel in the tank 10.

The aforementioned pulsed AC excitation of the transducer 14 may continue for a period of time to collect an adequate number of echo signals for signal processing thereof. Every so often, the generation of the first excitation signals is interrupted by the processor and switch 80 is controlled to its closed position to enable the second or DC excitation signal, which may be on the order of one milliamp, for example, generated from the source 44 to be conducted differentially over the twisted wire pair of the common conduction path 30 to the RTD 16. Note that the return current path from the RTD is to the ground reference of the source 44. The DC response voltage across the RTD that is representative of the temperature detected by the RTD is conducted back over the twisted wire pair to the interface circuit 38 wherein it is amplified by the amplifier 78 and conducted to the processor 46 via signal line 52 and A/D 54 for use along with the echo signals in determining the liquid level in the container 10. The DC excitation signal and response signal are blocked from interfering with the AC excitation circuitry by the capacitors C1 and C2. Once the processor 46 accepts the temperature measurement signal, it may return the switch 80 to its open position and continue controlling the oscillator circuit to generate the first excitation signals. In this manner, the interface circuit 38 is utilized to govern the conduction of the first and second excitation signals over the common conduction path 30 mutually exclusive of one another.

Thus, through the principles of the present invention, it is shown that an ultrasonic transducer and its temperature measuring device at a liquid container, like a fuel tank of an aircraft, for example, may share the same remotely located electronics on-board the aircraft for excitation and signal processing and share a common conduction path therebetween, thus affording a substantial savings in volume and weight as well as cost of labor, maintenance and fuel consumption. While the present invention has been presented here above in connection with a preferred embodiment, it is understood that modifications and equivalent substitutions may be made thereto without deviating from the broad principles thereof. Accordingly, the present invention should not be limited to any single embodiment, but rather construed in breadth and broad scope in accordance with the recitation of the appended claims hereto.

What is claimed is:

1. A liquid measurement system comprising:

an ultrasonic transducer disposed at a container of liquid for measuring the level of liquid in the container, said ultrasonic transducer being excited to generate ultrasonic pulses directed at the liquid level and for receiving ultrasonic echoes from the liquid level that are converted into corresponding echo signals;

a temperature measuring device disposed in contact with the liquid of the container in close proximity to said ultrasonic transducer, said temperature measuring device being excited to generate a response signal representative of the temperature of the liquid in close proximity to said ultrasonic transducer;

first means remotely located from the liquid container for generating first excitation signals for said ultrasonic transducer;

second means remotely located from the liquid container for generating second excitation signals for said temperature measuring device;

a common conduction path coupled to both of said ultrasonic transducer and said temperature measuring device for conducting said first excitation signals to said ultrasonic transducer and said corresponding echo signals therefrom, and for conducting said second excitation signals to said temperature measuring device and said response signals therefrom;

an interface circuit remotely located from the liquid container and coupled between said first and second means and said common conduction path for governing the conduction of said first and second excitation signals over the common conduction path and for providing a balanced interface for receiving both of said echo signals and response signals from the common conduction path; and processing means coupled to said interface circuit for receiving said echo signals and said response signals therefrom for determining liquid level in the container based on said received signals.

2. The liquid measuring system of claim 1 wherein the first means includes means for generating a differential first excitation signal; wherein the second means includes means for generating a differential second excitation signal; wherein the common conduction path includes a twisted wire pair; and wherein the ultrasonic transducer and temperature measuring device are coupled in parallel across said twisted wire pair at the liquid container.

3. The liquid measuring system of claim 1 wherein the ultrasonic transducer and temperature measuring device are contained in a common assembly coupled to said common conduction path at the liquid container.

4. The liquid measuring system of claim 1 wherein the liquid container is a fuel tank on-board an aircraft; and wherein the first means, second means, interface circuit and processing means are located remote from the fuel tank on-board the aircraft.

5. The liquid measuring system of claim 1 wherein the first means includes means for generating a pulsed AC signal of a high frequency as the first excitation signal; wherein the second means includes means for generating a DC signal as the second excitation signal; and wherein the interface circuit includes a switch for conducting said DC signal over the conduction path in a first position and for providing a substantially balanced impedance to said pulsed AC signal in a second position.

6. The liquid measuring system of claim 5 wherein the processing means includes means for controlling the generation of first excitation signals of the first means and for operating the switch to its first and second positions.

7. The liquid measuring system of claim 5 wherein the interface circuit includes first circuitry for processing pulsed AC echo signals received from the ultrasonic transducer; second circuitry for processing DC response signals received from the temperature measuring device; and includes circuitry for blocking the DC excitation signal from interfering with said first circuitry and for blocking the pulsed AC excitation signal from interfering with the second circuitry.

8. The liquid measuring system of claim 7 wherein the blocking circuitry includes first capacitive means in series with the path of DC excitation and second capacitive means in parallel with the path of pulsed AC excitation.

9. The liquid measuring system of claim 1 wherein the temperature measuring device includes a resistance temperature device (RTD).

10. The liquid measuring system of claim 9 wherein the RTD is coupled in parallel with the ultrasonic transducer and acts as a bleed resistor to the ultrasonic transducer.

11. The liquid measuring system of claim 9 wherein the resistance of the RTD is substantially greater than the resistance of the conduction path.

12. The liquid measuring system of claim 9 wherein the RTD is substantially non-inductive.

13. The liquid measuring system of claim 12 wherein the RTD is of a semiconductor-based type.

14. The liquid measuring system of claim 1 wherein the interface circuit includes means for governing the conduction of the first and second excitation signals over the common conduction path mutually exclusive of one another.

15. The liquid measuring system of claim 1 wherein the first means includes means for generating a pulsed AC signal of a high peak to peak voltage as the first excitation signal; wherein the second means includes means for generating a DC current signal as the second excitation signal which induces a DC response signal of a substantially lower voltage from the temperature measuring device.

16. The liquid measuring system of claim 15 wherein the interface circuit includes first circuitry for processing pulsed AC echo signals received from the ultrasonic transducer; second circuitry for processing DC response signals received from the temperature measuring device; and includes circuitry for blocking the high voltage pulsed AC excitation signals from interfering with said first circuitry and second circuitry.

17. Interface apparatus for sharing the excitation and signal processing of an ultrasonic transducer remotely located therefrom at a liquid container and of a temperature measuring device disposed in close proximity to said ultrasonic transducer for measuring the temperature of the liquid threat, said ultrasonic transducer being excited to generate ultrasonic pulses directed at the liquid level in the container and for receiving ultrasonic echoes from the liquid level that are converted into corresponding echo signals, said temperature measuring device being excited to generate a response signal representative of the temperature of the liquid in close proximity to said ultrasonic transducer, said interface apparatus including:

first means for generating first excitation signals for said ultrasonic transducer;

second means for generating second excitation signals for said temperature measuring device;

a common conduction path coupled to both of said ultrasonic transducer and said temperature measuring device for conducting said first excitation signals to said ultrasonic transducer and said corresponding echo signals therefrom, and for conducting said second excitation signals to said temperature measuring device and said response signals therefrom; and an interface circuit coupled between said first and second means and said common conduction path for governing the conduction of said first and second excitation signals over the common conduction path and for providing a balanced interface for receiving both of said echo signals and response signals from the common conduction path.

18. The interface apparatus of claim 17 wherein the first means includes means for generating a differential first excitation signal; wherein the second means includes means for generating a differential second excitation signal; wherein the common conduction path includes a twisted wire pair for coupling the ultrasonic transducer and temperature measuring device in parallel thereacross at the liquid container.

19. The interface apparatus of claim 17 wherein the liquid container is a fuel tank on-board an aircraft; and wherein the first means, second means, and interface circuit are located remote from the fuel tank on-board the aircraft.

20. The interface apparatus of claim 17 wherein the first means includes means for generating a pulsed AC signal of a high frequency as the first excitation signal; wherein the second means includes means for generating a DC signal as the second excitation signal; and wherein the interface circuit includes a switch for conducting said DC signal over the conduction path in a first position and for providing a substantially balanced impedance to said pulsed AC signal in a second position.

21. The interface apparatus of claim 20 including a processing means for controlling the generation of first excitation signals of the first means and for operating the switch to its first and second positions.

22. The interface apparatus of claim 20 wherein the interface circuit includes first circuitry for processing pulsed AC echo signals received from the ultrasonic transducer; second circuitry for processing DC response signals received from the temperature measuring device; and circuitry for blocking the DC excitation signal from interfering with said first circuitry and for blocking the pulsed AC excitation signal from interfering with the second circuitry.

23. The interface apparatus of claim 22 wherein the blocking circuitry includes first capacitive means in series with the path of DC excitation and second capacitive means in parallel with the path of pulsed AC excitation.

24. The interface apparatus of claim 17 wherein the second means includes means for generating a second excitation signal for a temperature measuring device that includes a resistance temperature device (RTD).

25. The interface apparatus of claim 24 wherein the second means includes means for generating a second excitation signal for the RTD that is coupled in parallel with the ultrasonic transducer and acts as a bleed resistor to the ultrasonic transducer.

26. The interface apparatus of claim 24 wherein the resistance of the conduction path is substantially less than the resistance of the RTD.

27. The interface apparatus of claim 24 wherein the second means includes means for generating a second excitation signal for the RTD that is substantially non-inductive.

28. The interface apparatus of claim 24 wherein the second means includes means for generating a second excitation signal for the RTD that is of a semiconductor-based type.

29. The interface apparatus of claim 17 wherein the interface circuit includes means for governing the conduction of the first and second excitation signals over the common conduction path mutually exclusive of one another.

30. The interface apparatus of claim 17 wherein the first means includes means for generating a pulsed AC signal of a high peak to peak voltage as the first excitation signal; wherein the second means includes means for generating a DC current signal as the second excitation signal which induces a DC response signal of a substantially lower voltage from the temperature measuring device; and wherein the interface circuit includes first circuitry for processing pulsed AC echo signals received from the ultrasonic transducer; second circuitry for processing DC response signals received from the temperature measuring device; and circuitry for blocking the high voltage pulsed AC excitation signals from interfering with said first circuitry and second circuitry.

* * * * *

UNITED STATES PATENT AND TRADEMARK OFFICE
CERTIFICATE OF CORRECTION

PATENT NO. : 6,748,803 B1
DATED : June 15, 2004
INVENTOR(S) : Scott Robert Durkee and Bradley F. Eid It is certified that error appears in the above-identified patent and that said Letters Patent is hereby corrected as shown below:

Column 7,
Line 66, "threat" should read -- thereat --.

Signed and Sealed this

Twenty-eighth Day of December, 2004

JON W. DUDAS
*Director of the United States Patent and Trademark Office*